(12) United States Patent
Yeshurun et al.

(10) Patent No.: US 6,924,087 B2
(45) Date of Patent: Aug. 2, 2005

(54) POLYMER MICRONEEDLES

(75) Inventors: Yehoshua Yeshurun, Haifa (IL); Meir Hefetz, Mitzpe Harashim (IL); Erwin Berenschot, Winterswijk (NL); Meint de Boer, Enschede (NL); Dominique Maria Altpeter, Hengelo (NL); Garrit Boom, Vriezenveen (NL)

(73) Assignee: Nano Pass Technologies Ltd., Haifa (IL)

( * ) Notice: Subject to any disclaimer, the term of this patent is extended or adjusted under 35 U.S.C. 154(b) by 38 days.

(21) Appl. No.: 10/397,359

(22) Filed: Mar. 27, 2003

(65) Prior Publication Data
US 2004/0072105 A1 Apr. 15, 2004

(30) Foreign Application Priority Data
Oct. 13, 2002 (IL) .............................................. 152271

(51) Int. Cl.$^7$ .......................... A61M 5/32; A61M 5/158
(52) U.S. Cl. ...................... 430/313; 430/312; 430/314; 430/966; 264/632; 264/643; 438/42; 438/43; 604/264; 604/272
(58) Field of Search ............................... 430/313, 312, 430/314, 966; 264/632, 643; 438/42, 43; 604/264, 272

(56) References Cited

U.S. PATENT DOCUMENTS

| | | | |
|---|---|---|---|
| 3,964,482 A | | 6/1976 | Gerstel et al. |
| 6,093,520 A | * | 7/2000 | Vladimirsky et al. ....... 430/326 |
| 6,334,856 B1 | * | 1/2002 | Allen et al. .................. 604/191 |
| 2002/0155737 A1 | * | 10/2002 | Roy et al. ..................... 439/66 |

* cited by examiner

Primary Examiner—John A. McPherson
Assistant Examiner—Daborah Chacko-Davis
(74) Attorney, Agent, or Firm—Mark M. Friedman

(57) ABSTRACT

A method for producing microneedles. The method including disposing a first layer of a radiation sensitive polymer on to a working surface and selectively irradiating the first layer such that the first layer has at least one irradiated region and at least one non-irradiated region. The method also including developing the first layer so as to selectively remove one of the at least one irradiated region and the at least one non-irradiated region such that, at least part of at least one remaining region at least partially defines a form of at least part of a microneedle structure. A microneedle structure including a plurality of microneedles at least partially formed from a radiation sensitive polymer.

26 Claims, 8 Drawing Sheets

POLYMER MICRONEEDLES

This application claims priority from Israeli application no. 152,271 filed 13 Oct. 2002.

FIELD AND BACKGROUND OF THE INVENTION

The present invention relates to microneedles and, in particular, it concerns microneedles formed from radiation sensitive materials.

Microneedles have been known for many years, first being taught by U.S. Pat. No. 3,964,482 to Gerstel, filed June 1976. However commercialization of microneedle technology has been difficult due to lack of an inexpensive production method as well as difficulty in finding suitable production materials which produce strong microneedles that will overcome tissue penetration problems and that will not break easily. Polymer microneedle production currently employs techniques using molds to form the needle structure. These methods have inherent difficulties relating to the formation of hollow microneedles and thus are less useful for fluid transfer. Prior art methods are typically expensive and the produced microneedles are relatively fragile. Generally, prior art microneedles used in transdermal applications are not robust enough and therefore break upon entering the skin or the microneedles are not sharp enough and thus do not penetrate the skin effectively.

Therefore there is a need for a method to produce an inexpensive, robust, sharp, hollow as well as non-hollow array of microneedles, typically for drug delivery and diagnostics.

SUMMARY OF THE INVENTION

The present invention is a polymer microneedle construction and method of production thereof.

According to the teachings of the present invention there is provided, a method for producing microneedles, comprising the steps of: (a) disposing a first layer of a radiation sensitive polymer on to a working surface; (b) selectively irradiating the first layer such that the first layer has at least one irradiated region and at least one non-irradiated region; and (c) developing the first layer so as to selectively remove one of the at least one irradiated region and the at least one non-irradiated region such that, at least part of at least one remaining region at least partially defines a form of at least part of a microneedle structure.

According to a further feature of the present invention, the at least part of the microneedle structure includes a plurality of at least partially formed microneedles.

According to a further feature of the present invention, each of at least two of the at least partially formed microneedles have a channel therein.

According to a further feature of the present invention, each of at least two of the at least partially formed microneedles have an oblique end surface.

According to a further feature of the present invention, at least two of the at least partially formed microneedles are different heights.

According to a further feature of the present invention, the at least part of the microneedle structure includes an at least partially formed microneedle having a channel therein.

According to a further feature of the present invention, the at least part of the microneedle structure includes an at least partially formed microneedle having an oblique end surface.

According to a further feature of the present invention, there is also provided, after the step of developing, the steps of: (a) disposing a filler at least partially around the at least one remaining region; (b) disposing a second layer of a radiation sensitive polymer on to: (i) at least part of the at least one remaining region; and (ii) at least part of the filler; (c) irradiating the second layer; and (d) developing the second layer such that, the second layer forms a base for at least part of the microneedle structure.

According to a further feature of the present invention, the base has at least one channel therein.

According to a further feature of the present invention, the step of irradiating the second layer is performed by selectively irradiating the second layer.

According to a further feature of the present invention, there is also provided the step of forming at least one groove in the working surface, such that the at least part of the microneedle structure is formed within the at least one groove, the at least one groove defining at least one oblique end surface of the microneedle structure.

According to a further feature of the present invention, the step of irradiating is performed using a light source producing visible light.

According to a further feature of the present invention, the step of irradiating is performed using ultraviolet light.

According to a further feature of the present invention, the step of irradiating is performed using a x-ray radiation.

According to a further feature of the present invention, there is also provided disposing a radiation source, which is used in the step of irradiating, and the working surface such that, the relative positioning of the radiation source and the working surface at least partially defining at least one oblique end surface of the microneedle structure.

According to the teachings of the present invention there is also provided, a microneedle structure, comprising a plurality of microneedles, each of the microneedles being at least partially formed from a radiation sensitive polymer.

According to a further feature of the present invention, a majority of each of the microneedles is formed from the radiation sensitive material.

According to a further feature of the present invention, there is also provided a substructure configured to form a base for the microneedles, the substructure being at least partially formed from a radiation sensitive polymer.

According to a further feature of the present invention, the substructure has at least one channel therein.

According to a further feature of the present invention, each of at least two of the microneedles have a channel therein.

According to a further feature of the present invention, each of at least two of the microneedles have an oblique end surface.

According to a further feature of the present invention, at least two of the microneedles are different heights.

According to the teachings of the present invention there is also provided, a microneedle structure, comprising a microneedle, the microneedle being at least partially formed from a radiation sensitive polymer, the microneedle having a channel therein.

According to a further feature of the present invention, a majority of the microneedle is formed from the radiation sensitive material.

According to the teachings of the present invention there is also provided, a microneedle structure, comprising a microneedle, the microneedle being at least partially formed from a radiation sensitive polymer, the microneedle having an oblique end surface.

According to a further feature of the present invention, a majority of the microneedles is formed from the radiation sensitive material.

According to the teachings of the present invention there is also provided, a method for producing microneedles, comprising the steps of: (a) disposing a layer of a material on to a working surface; and (b) processing the layer so as to selectively remove one of at least one irradiated region and at least one non-irradiated region, such that, at least part of at least one remaining region at least partially defines a form of at least part of a microneedle structure, wherein the processing includes a sub-step of selectively acting upon the layer with radiation so as to effect at least one of a physical and a chemical change selectively in material of the layer.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a polymer microneedle construction and method of production thereof.

The principles and method of production of the polymer microneedle construction according to the present invention may be better understood with reference to the drawings and the accompanying description.

A publication entitled "Process development for polymer needles by using SU-8 technology and silicon molding techniques" by Dominique Maria Altpeter of Mesa+ Institute, University of Twente, Enschede, Netherlands is incorporated by reference for all purposes as if fully set forth herein.

Figure 1:
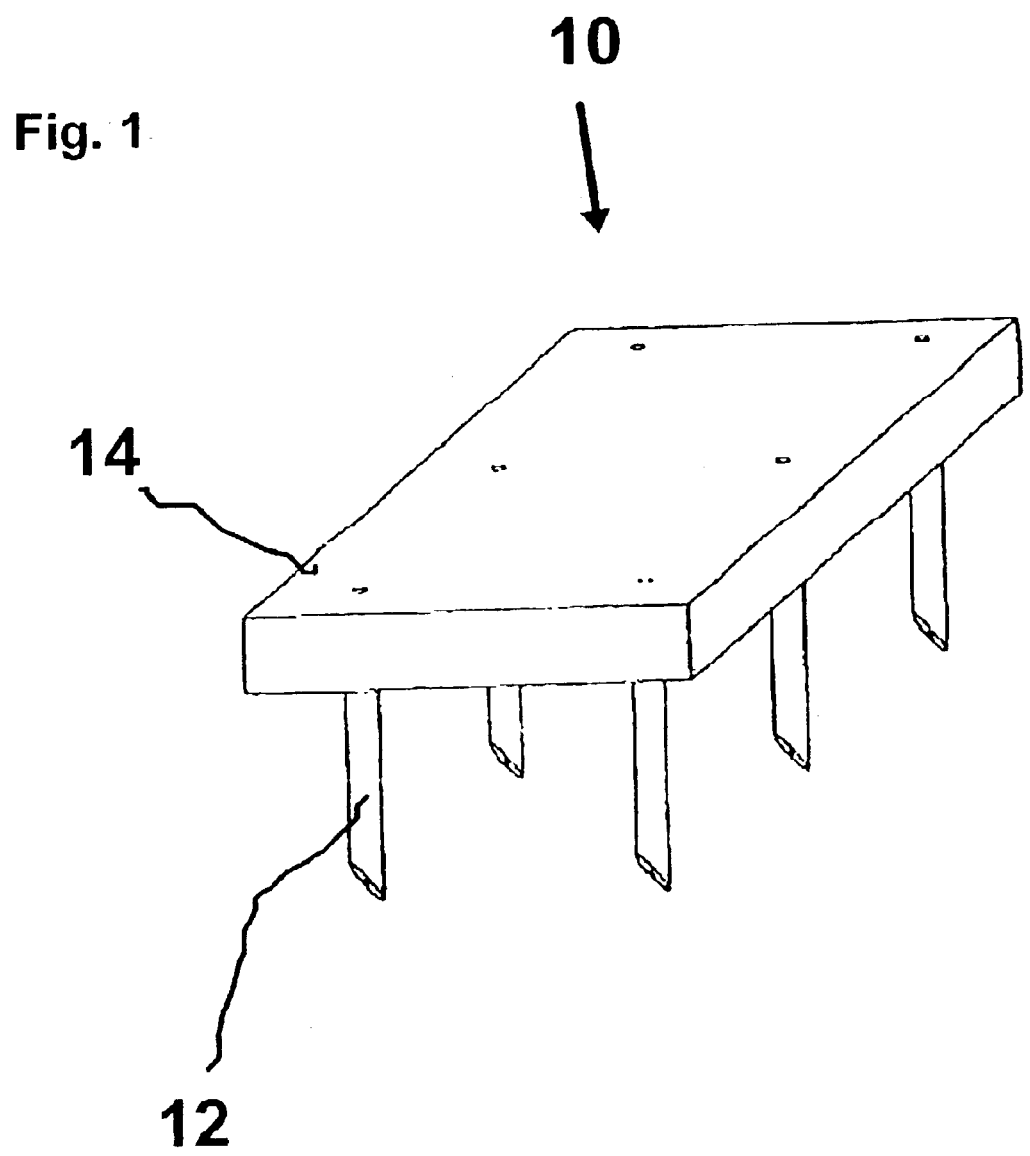
FIG. 1 is a schematic isometric view of a microneedle structure that is constructed and operable in accordance with a preferred embodiment of the present invention.

Reference is now made to FIG. 1, which is a schematic isometric view of a microneedle structure 10 that is constructed and operable in accordance with a preferred embodiment of the present invention. Microneedle structure 10 includes a plurality of microneedles 12 and a substructure 14 which acts as a base for microneedles 12. At least part of, and typically a majority of, each microneedle 12 and substructure 14 are formed from a radiation sensitive polymer, in that the form of microneedles 12 is typically wholly formed from a radiation sensitive material. Optionally, depending on the radiation sensitive polymer being used, microneedles 12 are coated with a material to make microneedles 12 biocompatible. Optionally, microneedles 12 are coated, using electrochemical techniques, with electrically conducting materials such as, titanium, gold and aluminum. These electrically conducting coated microneedles can be used for diagnosis, whereby microneedles 12 act as electrodes. Alternatively, these coated needles can be used to enhance drug delivery by employing electrophoresis by passing an electric current between microneedles 12. Radiation sensitive materials are discussed in more detail with respect to FIG. 10. Each microneedle 12 typically has a channel therein. However, it should be noted that optionally, microneedle 12 is formed without a channel therein. Substructure 14 typically has a channel therein for each channel of microneedles 12, such that therapeutic substances can be passed via the channels in substructure 14 through to the channels of microneedles 12 into the skin of the patient. Additionally, the channels can be used to remove biological fluids for sampling and/or collection from a patient. Additionally, each microneedle 12 has at least one oblique end surface giving microneedle 12 a sharp point for use in skin penetration. However, it should be noted that optionally, microneedle 12 is formed without an oblique end surface. Optionally, microneedles 12 of microneedle structure 10 are formed such that microneedles 12 have different heights. These and other features and their method of manufacture are described in more detail with respect to FIGS. 2 to 19.

Figure 2:
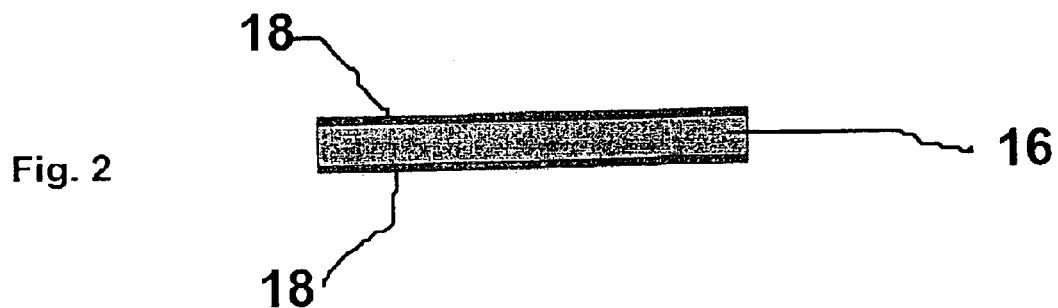
FIG. 2 is a schematic cross-sectional view of a wafer coated with a thin layer of Silicon Nitride that is used in the construction of the microneedle structure of FIG. 1.

Reference is now made to FIG. 2, which is a schematic cross-sectional view of a silicon wafer 16 coated with a thin layer of Silicon Nitride 18 that is used in the construction of microneedle structure 10 of FIG. 1. By way of introduction, wafer 16 is used as a working surface on which to form microneedle structure 10. At least one groove 20 (FIG. 7) is formed in wafer 16, such that said the end portion of microneedle 12 is formed within groove 20. Groove 20 defines the one or more oblique end surfaces of microneedle 12. The formation of groove 20 is described in more detail with respect to FIG. 2 to 7. Initially wafer 16 is cleaned to remove all dust and contamination. The cleaning is done with alcohol based materials and drying with air. Layer of Silicon Nitride 18 is disposed on wafer 16. The thickness of layer of Silicon Nitride 18 is typically 300 nanometers. This coating is performed using a LPCVD process. Layer of Silicon Nitride 18 is used later as a mask for wet etching (FIG. 6).

Figure 3:
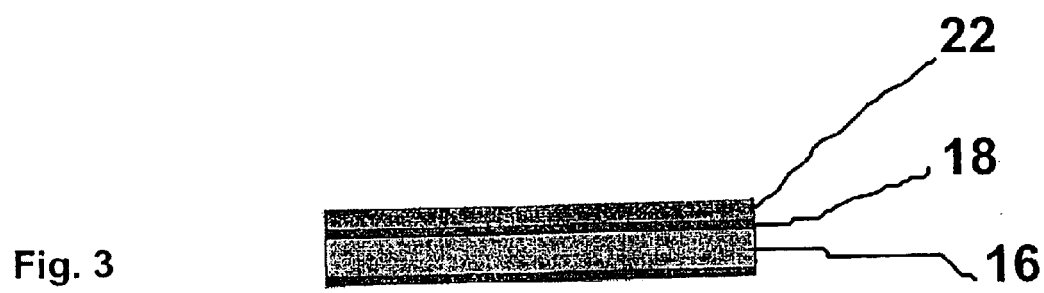
FIG. 3 is a schematic cross-sectional view of the wafer of FIG. 2 with a layer of photoresist coating the layer of Silicon Nitride.

Reference is now made to FIG. 3, which is a schematic cross-sectional view of wafer 16 of FIG. 2 after the following step is performed. A layer of photoresist 22 is coated on top of layer of Silicon Nitride 18. Materials suitable for layer of photoresist 22 are known to those skilled in the art.

Figure 4:
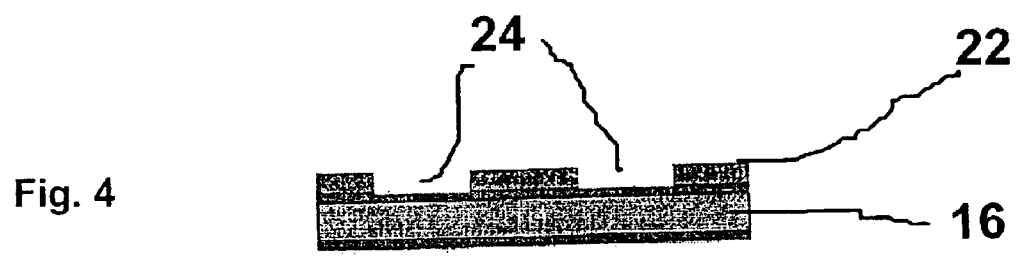
FIG. 4 is a schematic cross-sectional view of the wafer of FIG. 3 after a series of parallel strips have been formed on the layer of photoresist.

Reference is now made to FIG. 4, which is a schematic cross-sectional view of wafer 16 of FIG. 3 after the following steps are performed. Layer of photoresist 22 is exposed to light (photolithography process) through a KOH mask (not shown). The KOH mask is configured such that when layer of photoresist 22 is developed, a series of parallel strips 24 are formed on wafer 16 in layer of photoresist 22. Radiation sources suitable for this step as well as developing techniques are known to those skilled in the art.

Figure 5:
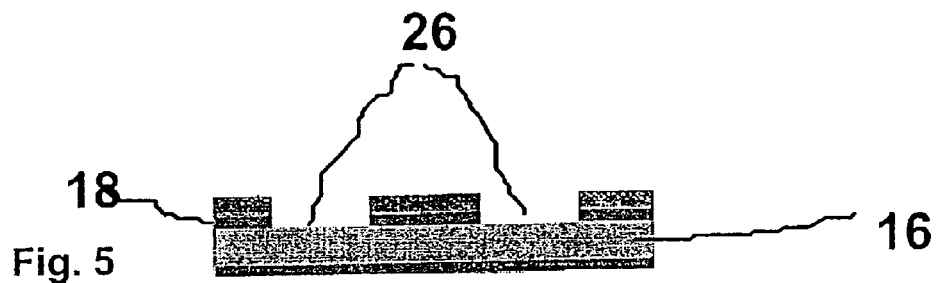
FIG. 5 is a schematic cross-sectional view of the wafer of FIG. 4 after plasma etching, creating a series of parallel in the Silicon nitride layer.
Figure 6:
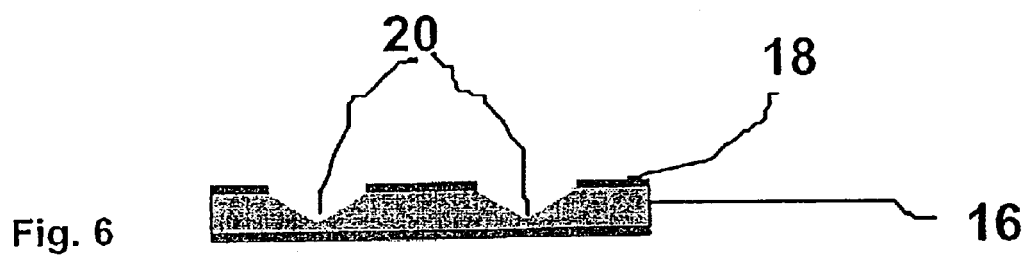
FIG. 6 is a schematic cross-sectional view of the wafer of FIG. 5 after wet etching creating grooves therein.

Reference is now made to FIG. 5, which is a schematic cross-sectional view of wafer 16 of FIG. 4 after the following step is performed. Plasma etching is performed creating a series of parallel strips 26 in layer of Silicon Nitride 18.

Reference is now made to FIG. 6, which is a schematic cross-sectional view of wafer 16 of FIG. 5 after the following step is performed. Wet etching of wafer 16 is performed creating grooves 20 at the locations of parallel strips 26 (FIG. 5) where there is no protective layer of Silicon Nitride 18. The wet etching process is performed by placing wafer 16 in a chemical bath for a short time. For example, by using chemicals such as THEMA or KOH. This wet etching process etches wafer 16 in its crystallographic plans to create grooves 20 in silicon wafer. As described above with respect to FIG. 2, groove 20 act as a working surface on which to form the tips of microneedles 12 to give the tips at least one oblique end surface.

Figure 7:
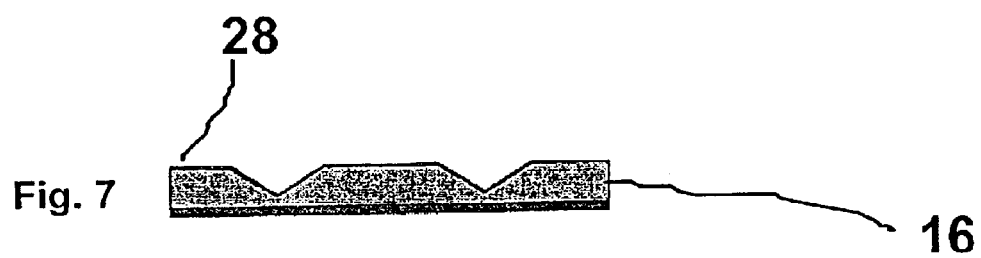
FIG. 7 is a schematic cross-sectional view of the wafer of FIG. 6 having a thin layer disposed Silicon Nitride thereon.

Reference is now made to FIG. 7, which is a schematic cross-sectional view of wafer 16 of FIG. 6 after the following steps are performed. A thin layer of Silicon Nitride 28 is now disposed thereon in order to protect wafer 16 during later stages where a KOH chemical is used. A layer of polysilicon (not shown) is then deposited on top of layer of Silicon Nitride 28 using a LPCVD process. This latter layer helps release of microneedle structure 10 from wafer 16 as will be described in more detail with respect to FIG. 19.

Figure 8:
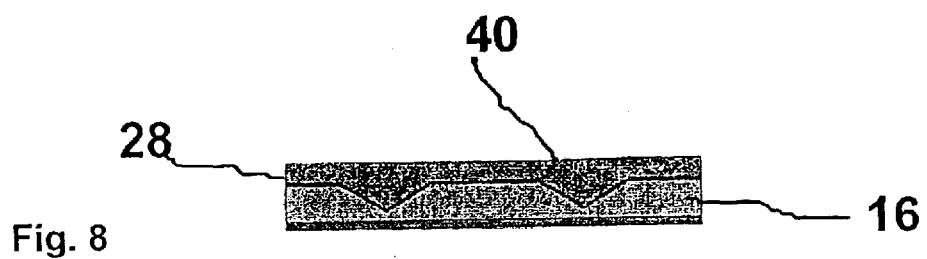
FIG. 8 is a schematic cross-sectional view of the wafer of FIG. 7 having a thick layer of photoresist spin coated thereon.

Reference is now made to FIG. 8, which is a schematic cross-sectional view of wafer 16 of FIG. 7 after the following step is performed. A thick layer of a radiation sensitive polymer 40 (photoresist), such as SU8, is disposed, typically by spin coating, on to the working surface of wafer 16 on top of layer of Silicon Nitride 28. Other examples suitable materials for layer of radiation sensitive polymer 40 are listed below in Table 1.

Figure 9:
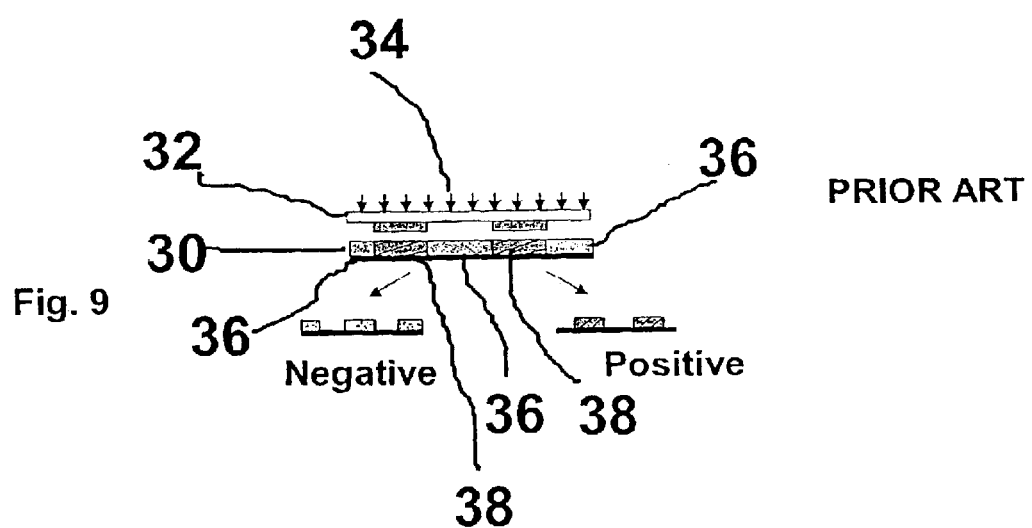
FIG. 9 is a schematic cross-sectional view of a layer of photoresist being irradiated through a mask in accordance with the prior art.

Reference is now made to FIG. 9, which is a schematic cross-sectional view of a layer of photoresist 30 being irradiated through a mask 32 in accordance with the prior art. Arrows 34 represent the radiation incident on mask 32. Irradiation through mask 32 creates irradiated regions 36 in layer of photoresist 30 and non-irradiated regions 38 in layer of photoresist 30. Developing of layer of photoresist 30 removes either irradiated regions 36 or non-irradiated regions 38 depending on whether layer of photoresist 30 is a positive or negative photoresist. If layer of photoresist 30 is a negative photoresist then non-irradiated regions 38 are removed on developing. If layer of photoresist 30 is a positive photoresist then irradiated regions 36 are removed on developing. It will be apparent to those ordinarily skilled in the art that the radiation sensitive polymer used in the method of the present invention is either positive or negative.

Figure 10:
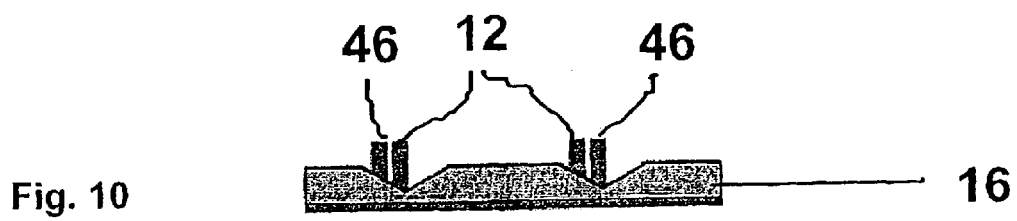
FIG. 10 is a schematic cross-sectional view of the wafer of FIG. 8 after selective irradiation and developing of the thick layer of photoresist, defining a form of microneedles.

Reference is now made to FIG. 10, which is a schematic cross-sectional view of wafer 16 of FIG. 8 after processing of layer of radiation sensitive polymer 40 (FIG. 9) defining a form of microneedles 12. This processing includes selectively acting upon layer of radiation sensitive polymer 40 with radiation so as to effect a physical and/or chemical change selectively in the material of layer of radiation sensitive polymer 40. This processing typically includes selective irradiation and developing of layer of radiation sensitive polymer 40. These steps are described in more detail below. First, layer of a radiation sensitive polymer 40 (FIG. 9) is selectively irradiated, typically using a mask, such that layer of radiation sensitive polymer 40 has one or more irradiated regions (not shown) and one or more non-irradiated regions (not shown). The irradiating is typically performed using a light source producing visible light, ultraviolet light or by x-ray radiation. It will be apparent to those skilled in the art that the radiation source depends on the material used for layer of radiation sensitive polymer 40. Other radiation sources and materials are known to those skilled in the art. It should be noted that a radiation insensitive material could be embedded with a radiation sensitive material (such as PDMS, Polydimethsiloxane and PCB) acting as a precursor to make the combined material react when exposed to a radiation source. The term "radiation sensitive material" used in the claims includes combined materials which are sensitive to a radiation source.

Table 1, below, is an example of suitable radiation sources and their corresponding radiation sensitive materials.

| Radiation Source | Materials |
| --- | --- |
| Ion Radiation (Xenon) | Polyimide (such as PI2732 by DuPont) |
| UV or near UV | Epoxy based materials such as SU8, BenzoCycloBute (BCB), Polynorbornenes (made by B F Goodrich), UV polymer- PVK |
| X-ray | PMMA |
| Electron beam | PMMA |
| Light | Photoresist materials such as Poly(Benzoxazole) BPO, PDMS (Polydimethsiloxane) |
| Laser | Photoresist materials such as PBO |

It should be noted that PDMS, PMMA and BCB are biocompatible as well as being used in the microfabrication technology and are therefore very suited to microneedle manufacture.

After layer of radiation sensitive polymer 40 is exposed to the radiation, a post exposure bake is performed on layer of radiation sensitive polymer 40. Then, layer of radiation sensitive polymer 40 is developed so as to selectively remove either the irradiated regions or non-irradiated regions of layer of radiation sensitive polymer 40, depending on the type of polymer used (positive or negative) such that, at least part of one or more remaining regions 46 at least partially defines a form of at least part of microneedles 12. The developing process is described as defining "a form" of at least part of microneedles 12 in that further processing is typically needed to make microneedles 12 usable. Remaining regions 46 are then rinsed and dried and then generally baked. The above process defines the outer surface of microneedle 12 as well as the surface of the channel within microneedle 12. It will be appreciated by those skilled in the art that the above process may be used to create one or more microneedles with or without channels therein. It will also be appreciated by those skilled in the art that the above process may be used to create one or more microneedles with or without one or more oblique end surfaces. The steps described with respect to FIGS. 8 and 10 are repeated as necessary depending on the height of microneedles required.

Figure 11:
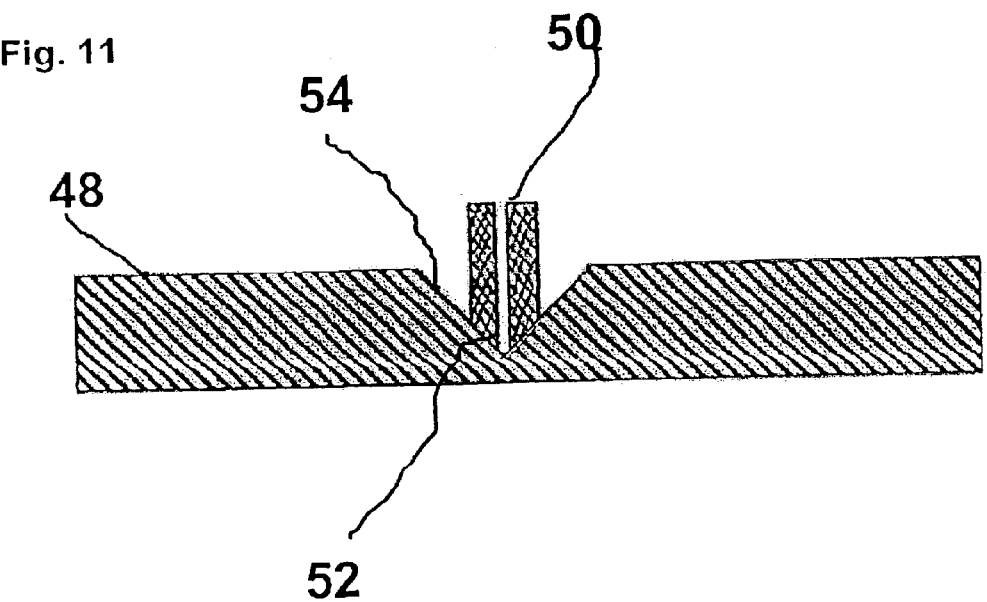
FIG. 11 is a schematic cross-sectional view of a wafer having a microneedle disposed thereon, the microneedle having two oblique end surfaces that is constructed and operable in accordance with a first alternate embodiment of the present invention.

Reference is now made to FIG. 11, which is a schematic cross-sectional view of a wafer 48 having a microneedle 50 disposed thereon that is constructed and operable in accordance with a first alternate embodiment of the present invention. Microneedle 50 has two oblique end surfaces 52. Oblique end surfaces 52 are defined by forming microneedle 50 at the middle of a groove 54 in the surface of wafer 48.

Figure 12:
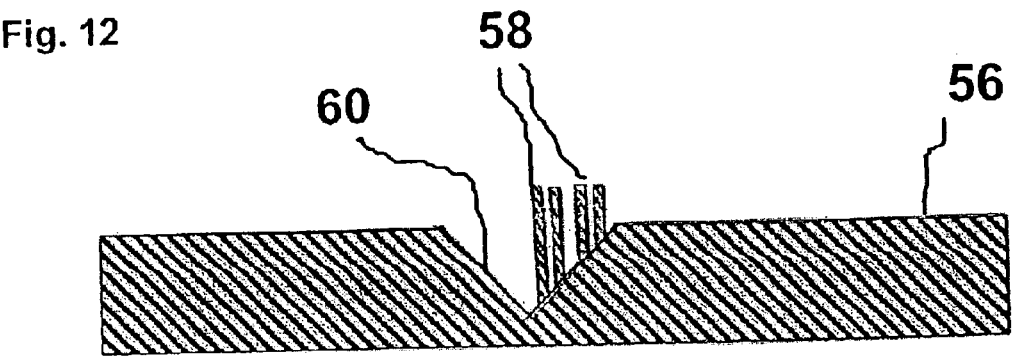
FIG. 12 is a schematic cross-sectional view of a wafer having two microneedles disposed thereon, the microneedles being different heights that is constructed and operable in accordance with a second alternate embodiment of the present invention.

Reference is now made to FIG. 12, which is a schematic cross-sectional view of a wafer 56 having two microneedles 58 disposed thereon that is constructed and operable in accordance with a second alternate embodiment of the present invention. Wafer 56 has a groove 60 in the surface of wafer 56. Microneedles 58 are formed at differing locations on groove 60 such that microneedles 58 have different heights. Microneedle arrays having microneedles of different heights are known as three-dimensional microneedle arrays. Three-dimensional microneedle arrays provides a three-dimensional dispersion of injected substances for drug delivery applications as well as enhanced sampling efficacy for diagnostic applications.

Figure 13:
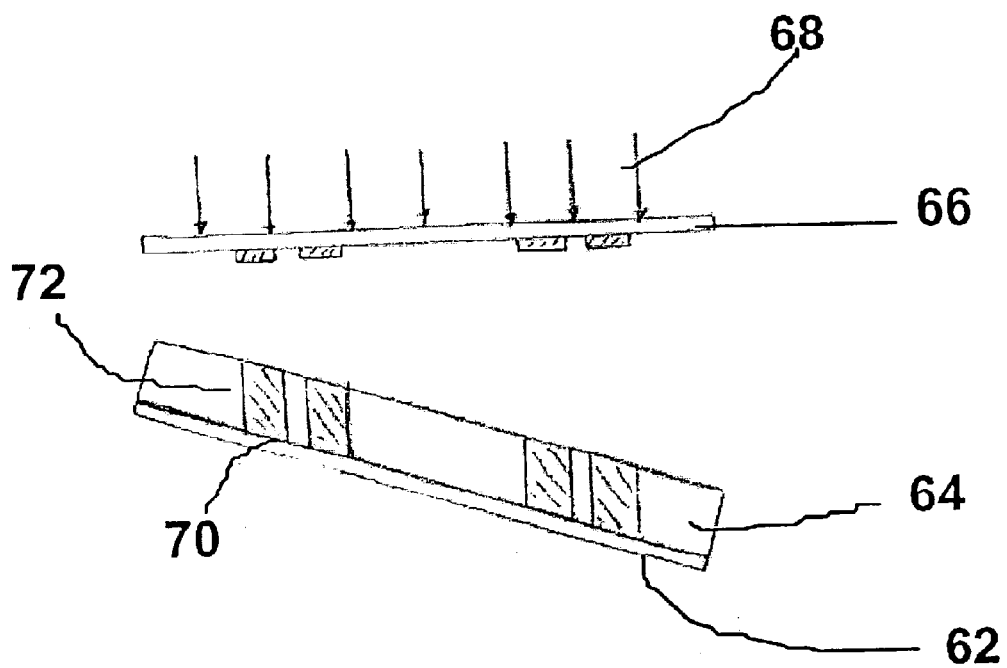
FIG. 13 is a schematic cross-sectional view of a wafer having a thick layer of photoresist disposed thereon being selectively irradiated by a radiation source wherein the relative positioning of the radiation source and the wafer at least partially defines the oblique end surface of each microneedle that is constructed and operable in accordance with a third alternate embodiment of the present invention.

Reference is now made to FIG. 13, which is a schematic cross-sectional view of a wafer 62 having a thick layer of photoresist 64 disposed thereon being selectively irradiated by a radiation source (not shown) through a mask 66 that is constructed and operable in accordance with a third alternate embodiment of the present invention. Wafer 62 typically has a substantially flat surface. Incident radiation is represented by arrows 68. The relative positioning of the radiation source and wafer 62 at least partially defines an oblique end surface 70 of a microneedle 72. The relative positioning of the radiation source and wafer 62 is described as "at least partially defines" in that if the surface of wafer 62 is not flat then the contours of the surface of wafer 62 will also define oblique end surface 70 of microneedle 72.

Figure 14:
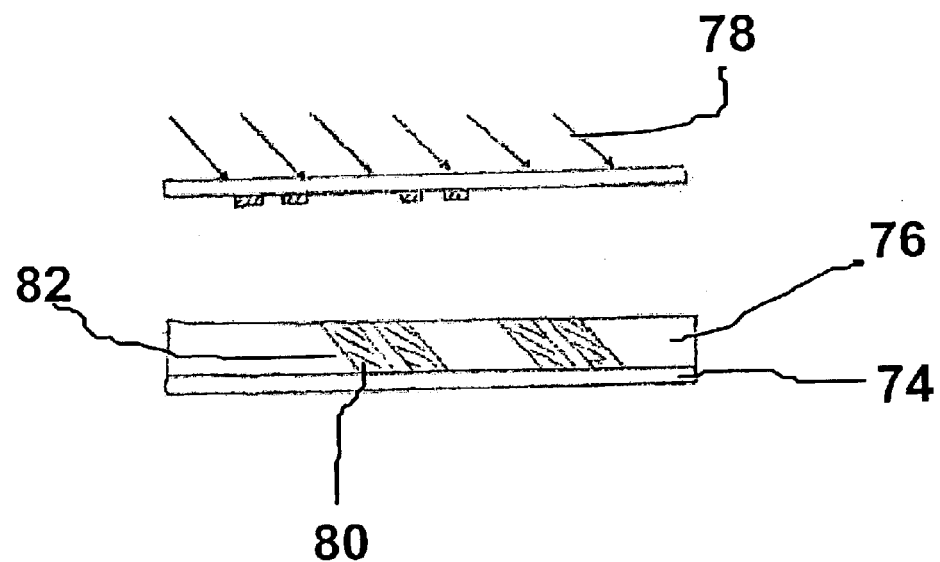
FIG. 14 is a schematic cross-sectional view of a wafer having a thick layer of photoresist disposed thereon being selectively irradiated by a radiation source wherein the relative positioning of the radiation source and the wafer at least partially defines the oblique end surface of each microneedle that is constructed and operable in accordance with a fourth alternate embodiment of the present invention.

Reference is now made to FIG. 14, which is a schematic cross-sectional view of a wafer 74 having a thick layer of photoresist 76 disposed thereon being selectively irradiated by a radiation source (not shown) that is constructed and operable in accordance with a fourth alternate embodiment of the present invention. Incident radiation is represented by arrows 78. The relative positioning of the radiation source and wafer 74 at least partially defines an oblique end surface 80 of each microneedle 82. The examples of both FIG. 13 and FIG. 14 have been brought to show that the relative positioning of the radiation source and the wafer define the shape of the end of the microneedles. The orientation of the mask defines the width of the microneedles.

Figure 15:
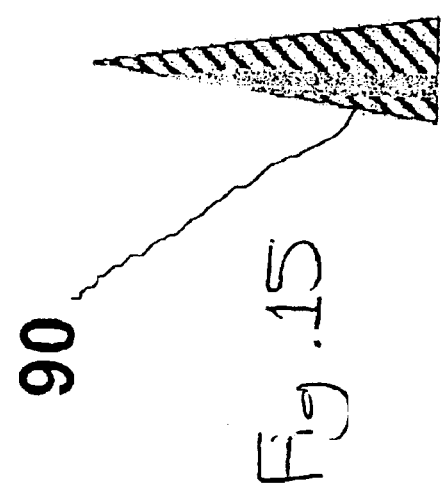
FIG. 15 is a schematic cross-sectional view of possible microneedle structures that is constructed and operable in accordance with a fifth alternate embodiment of the present invention.
Figure 15:
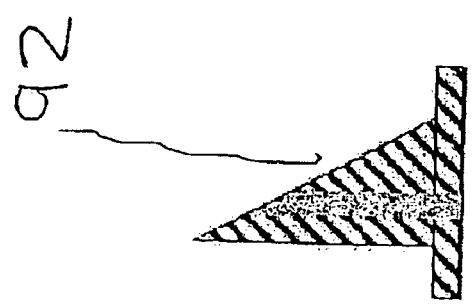
Figure 15:
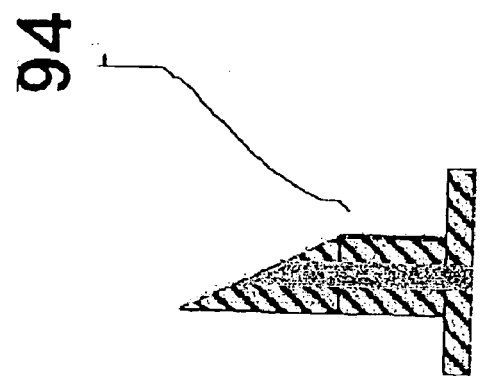

Reference is now made to FIG. 15, which is a schematic cross-sectional view of possible microneedle structures that is constructed and operable in accordance with a fifth alternate embodiment of the present invention. It will be appreciated by those skilled in the art that the shape of the microneedle including the outside shape as well as the shape of the inner channel is unlimited. These shapes are only based upon the configuration of the mask, the relative positioning of the radiation source and the working surface, as well as the shape of the working surface. Typical shapes include tubes, pyramids and cones with or without channels. Microneedles 90, 92, 94 have channels which are not aligned with the tip of the needle. Therefore, if a greater flow of fluids is needed, the channels can be enlarged without effecting the size of the tip or the forces needed for skin penetration. Additionally, the fact that the structure and position of the tip can be manipulated allows for developing discrete applications, such as using needles for piercing, cutting and fixing arrays on tissue. The microneedle structure can be configured to meet the requirements of various types of applications. By way of a first example, drug delivery requires sharp needles to make holes. By way of a second example, balloon mounted microneedles need cutting knife or blade-type tips. By way of a third example, vaccination applications may require enlargement of the surface area of the penetrating object necessitating making jagged edged tips and channels.

Figure 16:
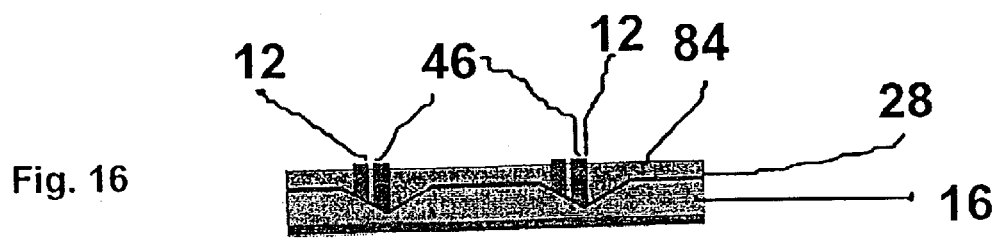
FIG. 16 is a schematic cross-sectional view of the wafer of FIG. 10 having a filler layer of a polymer resist material disposed thereon surrounding the microneedles.

Reference is now made to FIG. 16, which is a schematic cross-sectional view of wafer 16 of FIG. 10 after the following step is performed. A filler layer 84 of a polymer resist material is disposed at least partially, typically completely, around remaining regions 46. The term "around" includes around the outside of microneedles 12 as well as in the channel of microneedles 12. Filler layer 84 acts as a filling material on which to build substructure 14 (FIG. 1). Filler layer 84 extends from layer of Silicon Nitride 28 to just below the base of microneedles 12. Optionally filler layer 84 is used to define the length of microneedles 12.

Figure 17:
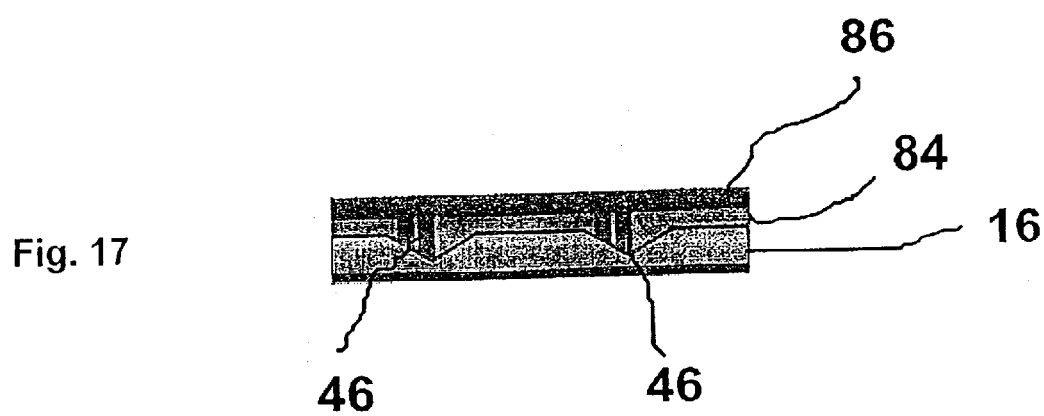
FIG. 17 is a schematic cross-sectional view of the wafer of FIG. 16 having a spin coated layer of photoresist disposed on top of the resist material and the microneedles.

Reference is now made to FIG. 17, which is a schematic cross-sectional view of wafer 16 of FIG. 16 after the following step is performed. A layer of radiation sensitive polymer 86, such as SU8, is disposed, typically by spin coating, on top of filler layer 84 and remaining regions 46 (microneedles 12).

Figure 18:
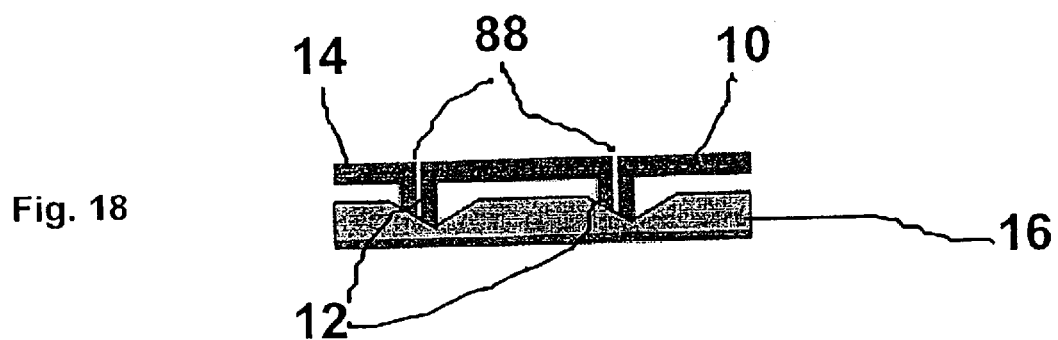
FIG. 18 is a schematic cross-sectional view of the wafer of FIG. 17 after selectively irradiating and developing the layer of photoresist to define a base for the microneedles.

Reference is now made to FIG. 18, which is a schematic cross-sectional view of wafer 16 of FIG. 17 after the following steps are performed. Layer of radiation sensitive polymer 86 (FIG. 17) is selectively irradiated, typically using a mask (not shown). This mask is configured to define a form of channels 88 in substructure 14 which join up with the channels in microneedles 12. Then, layer of radiation sensitive polymer 86 is developed such that layer of radiation sensitive polymer 86 forms a base for microneedle structure 10. Generally, layer of radiation sensitive polymer 86 is baked after the developing step.

Figure 19:
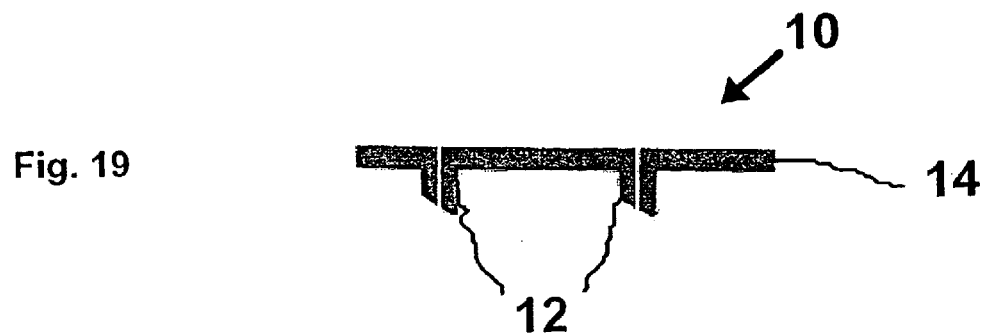
FIG. 19 is a schematic cross-sectional view of the microneedles and the base of FIG. 18 after being released from the wafer.

Reference is now made to FIG. 19, which is a schematic cross-sectional view of microneedle structure 10 having microneedles 12 and substructure 14 of FIG. 18 after the following step is performed. Microneedle structure 10 is released from wafer 16 (FIG. 18) using a KOH etching material.

The above method has been described with reference to using a radiation sensitive polymer to form microneedles 12, typically using a process including the steps of selective irradiation, developing and baking. It will be appreciated by those skilled in the art that some of these processing steps may not be needed depending on the chosen radiation sensitive polymer. It will also be appreciated by those skilled in the art that, optionally, microneedle 12 are formed at least partially using micro-ablation techniques. For example, but not limited to, the form of microneedles 12 being defined by selectively irradiating a material using a high power radiation source which ablates unwanted material, leaving behind the form of microneedles 12.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art which would occur to persons skilled in the art upon reading the foregoing description.

What is claimed is:

1. A method for producing microneedles, comprising the steps of:
    (a) providing a working surface; and
    (b) forming a polymer microneedle structure by performing a set of steps in order, a plurality of times, said set of steps including the steps of:
        (i) disposing a layer of a radiation sensitive polymer on to said working surface; then
        (ii) selectively irradiating said layer such that said layer has at least one irradiated region and at least one non-irradiated region; and then
        (iii) developing said layer so as to selectively remove one of said at least one irradiated region and said at least one non-irradiated region such that, at least part of at least one remaining region of said polymer forms a part of a microneedle structure.

2. The method of claim 1, wherein said at least part of said microneedle structure includes a plurality of at least partially formed microneedles.

3. The method of claim 2, wherein each of at least two of said at least partially formed microneedles have a channel therein.

4. The method of claim 2, wherein each of at least two of said at least partially formed microneedles have an oblique end surface.

5. The method of claim 2, wherein at least two of said at least partially formed microneedles are different heights.

6. The method of claim 1, wherein said at least part of said microneedle structure includes an at least partially formed microneedle having a channel therein.

7. The method of claim 1, wherein said at least part of said microneedle structure includes an at least partially formed microneedle having an oblique end surface.

8. The method of claim 1, further comprising, after said step of developing, the steps of:
    (a) disposing a filler at least partially around said at least one remaining region;
    (b) disposing a second layer of a radiation sensitive polymer on to: (i) at least part of said at least one remaining region; and (ii) at least part of said filler;
    (c) irradiating said second layer; and
    (d) developing said second layer such that, said second layer forms a base for at least part of said microneedle structure.

9. The method of claim 8, wherein said base has at least one channel therein.

10. The method of claim 8, wherein said step of irradiating said second layer is performed by selectively irradiating said second layer.

11. The method of claim 1, further comprising the step of forming at least one groove in said working surface, such that said at least part of said microneedle structure is formed within said at least one groove, said at least one groove defining at least one oblique end surface of said microneedle structure.

12. The method of claim 1, wherein said step of irradiating is performed using a light source producing visible light.

13. The method of claim 1, wherein said step of irradiating is performed using ultraviolet light.

14. The method of claim 1, wherein said step of irradiating is performed using a x-ray radiation.

15. The method of claim 1, further comprising disposing a radiation source, which is used in said step of irradiating, and said working surface such that, the relative positioning of said radiation source and said working surface at least partially defining at least one oblique end surface of said microneedle structure.

16. A microneedle structure, comprising a plurality of microneedles, each of said microneedles being at least partially formed from a radiation sensitive polymer, wherein at least two of said microneedles are different heights.

17. The structure of claim 16, wherein a majority of each of said microneedles is formed from said radiation sensitive material.

18. The structure of claim 16, further comprising a substructure configured to form a base for said microneedles, said substructure being at least partially formed from a radiation sensitive polymer.

19. The structure of claim 18, wherein said substructure has at least one channel therein.

20. The structure of claim 16, wherein each of at least two of said microneedles have a channel therein.

21. The structure of claim 16, wherein each of at least two of said microneedles have an oblique end surface.

22. A microneedle structure, comprising a microneedle, said microneedle being at least partially formed from a radiation sensitive polymer, said microneedle having a channel therein.

23. The microneedle structure of claim 22, wherein a majority of said microneedle is formed from said radiation sensitive material.

24. A microneedle structure, comprising a microneedle, said microneedle being at least partially formed from a radiation sensitive polymer, said microneedle having an oblique end surface.

25. The microneedle structure of claim 24, wherein a majority of said microneedles is formed from said radiation sensitive material.

26. A method for producing microneedles, comprising the steps of:
(a) providing a working surface; and
(b) forming a polymer microneedle structure by performing a set of steps in order, a plurality of times, said set of steps including the steps of:
(i) disposing a layer of a material on to a working surface; and then
(ii) processing said layer so as to selectively remove one of at least one irradiated region and at least one non-irradiated region of said layer, such that, at least part of at least one remaining region of said material at least partially forms a part of a microneedle structure, wherein said processing includes a sub-step of selectively acting upon said layer with radiation so as to effect at least one of a physical and a chemical change selectively in said material of said layer.

* * * * *